United States Patent [19]

Steinberg et al.

[11] Patent Number: 4,463,210
[45] Date of Patent: Jul. 31, 1984

[54] PRODUCTION OF CHEMICAL FEEDSTOCK BY THE METHANOLYSIS OF WOOD

[75] Inventors: Meyer Steinberg, Melville; Peter Fallon, East Moriches, both of N.Y.

[73] Assignee: The United States of America as represented by the United States Department of Energy, Washington, D.C.

[21] Appl. No.: 500,101

[22] Filed: Jun. 1, 1983

[51] Int. Cl.³ .............................................. C07C 1/00
[52] U.S. Cl. ................................. 585/469; 48/209; 201/20; 201/21; 201/28; 585/240; 585/408; 585/638; 585/733; 585/943
[58] Field of Search ............... 585/240, 408, 469, 638, 585/733, 943; 201/8, 20, 21, 28; 48/209

[56] References Cited
U.S. PATENT DOCUMENTS 1,976,591 10/1934 Wagner ................................. 585/943
2,061,597 11/1936 Smith et al. .......................... 585/943
3,993,457 11/1976 Cahn et al. ............................ 48/209
4,064,018 12/1977 Choi ....................................... 201/28
4,313,011 1/1982 Weil et al. ............................... 201/8

OTHER PUBLICATIONS

Steinberg et al., Flash Pyrolysis and Hydropyrolysis of Biomass (Progress Report No. 2), Oct. 1981, presented at the 13th Biomass Thermochemical Conversion Contractors Meeting, Oct. 25-27, 1981, Arlington, Va., (Budget Reporting Code EB-02-02).

Primary Examiner—Delbert E. Gantz
Assistant Examiner—A. Pal
Attorney, Agent, or Firm—Margaret C. Bogosian; James W. Weinberger; Michael F. Esposito

[57] ABSTRACT

A process for the production of ethylene, benzene and carbon monoxide from particulated biomass such as wood by reaction with methane at a temperature of from 700° C. to 1200° C., at a pressure of from 20 psi to 100 psi for a period of from 0.2 to 10 seconds.

10 Claims, 1 Drawing Figure

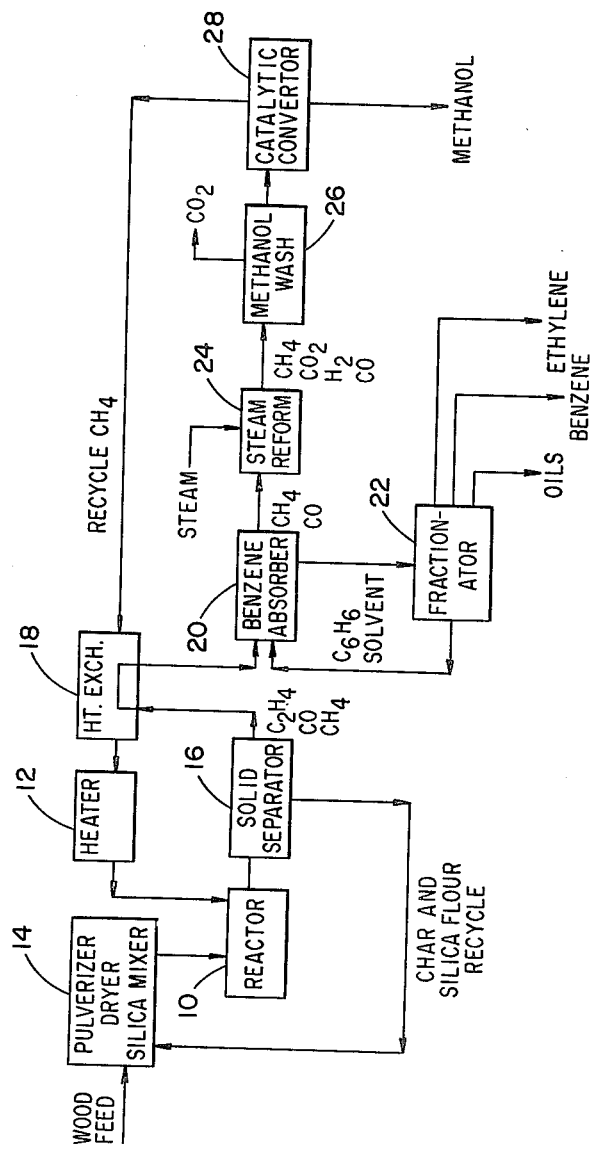

PRODUCTION OF CHEMICAL FEEDSTOCK BY THE METHANOLYSIS OF WOOD

BACKGROUND OF THE INVENTION

The U.S. Government has rights in this invention pursuant to Contract No. DE-AC02-76 CH 00016 between the U.S. Department of Energy and Associated Universities, Inc.

This invention relates to the production of chemical feedstock from biomass, especially wood.

With the advent of the "energy crisis" and the concommitant realization of the generally limited nature of oil and natural gas supplies for conversion to energy or petrochemicals, and particularly the uncertain nature of Mid-Eastern oil supplies, numerous efforts were begun to develop methods to utilize domestic resources such as coal and wood as substitutes for scarce and uncertain oil and gas supplies. Coal is an attractive resource because there are huge natural deposits within continental United States. Wood is attractive not only because of abundant supply, but also because it is renewable.

It is an object of this invention to provide methods for the production of chemical feedstocks from biomass and natural gas.

It is a further object of this invention to provide methods for the production of ethylene, benzene, toluene, xylene and carbon monoxide in substantial amounts from wood and methane which are both facile and economical.

BRIEF SUMMARY OF THE INVENTION

The above objects are achieved by the low pressure process of the subject invention which comprises the steps of reacting particulate wood with methane at a temperature of from about 700° C. to 1200° C. at a pressure from about 20 psi to 100 psi for a period less than 10 seconds. The preferred parameters for best yields of products and economy of operation are 900° C. to 1000° C. for a reaction period of from 0.2 to 5 seconds at a pressure of 30 psi to 60 psi.

The conversion process is followed by rapid cooling to temperatures under 300° C. to stabilize the products.

The invention will be described with particular emphasis on wood. It will be recognized, however, that it is applicable to biomass in general such as cellulosic products and agricultural waste. No specific species of wood are required.

Surprisingly, it has been found that in accordance with the practice of this invention yields of over 20% ethylene and 12% benzene together with more than 45% carbon monoxide are achieved with apparently no net consumption of methane. The subject invention advantageously provides for the conversion of a renewable source material to economically significant quantities of important industrial chemicals.

BRIEF DESCRIPTION OF THE DRAWINGS

The FIGURE is a block diagram of a chemical process in accordance with the method of the subject invention which shows also a specific embodiment of the invention in which the carbon monoxide produced is converted to methanol.

DETAILED DESCRIPTION OF A PREFERRED EMBODIMENT OF THE INVENTION

Turning to the FIGURE, there is shown a process of the invention. Biomass particulates, such as wood in a particle size range up to about 6 mm, preferably 0.1 to 5 mm, are introduced into reactor 10. The wood may be used alone but, especially in small reactors, it is preferable to introduce it in admixture with an inert particulate material to inhibit caking. Any of a number of heat resistant caking inhibitors can be employed. Typically, they will be of a particle size range comparable with the wood. The presently preferred caking inhibitor is silica powder, but other materials such as sand and aluminum oxide can also be employed.

Methane gas which may contain minor amounts of other constituents heated in conventional heater 12 to a temperature of from 700° C. to 1200° C., preferably 900° C. to 1000° C. is fed into reactor 10 and reacted with the wood particulates at a pressure of from 20 psi to 100 psi for a period of from 0.2 to 10 seconds, preferably 0.2 to 5 seconds.

It is convenient, but not necessary, to feed the wood-silica mixture to reactor 10 from unit 14 wherein the wood is pulverized and mixed with the silica. The mixture may also be concurrently dried so that the moisture content of the wood is kept to a minimum. With green wood it is highly desirable to reduce the moisture content, but with aged wood which has been protected from atmospheric moisture the predrying is often unnecessary. In any event, it is generally preferred that the moisture content of the wood be no more than 3% by weight.

Reactor 10 may be any conventional type reactor vessel capable of providing the desired reaction conditions. The presently preferred reactor is a parallel flow tubular reactor, but a fluid bed reactor may also be conveniently employed.

The solids, char and silica flour are separated from the effluent gas stream in solid separator 16. The separator may be any of several such devices well known to those skilled in the art. Cyclones or other centrifugal devices are especially useful, but gravity separators may also be employed.

The wood leaves very little ash, so the solids from the separator comprising principally char and silica may be recycled to the pulverizing unit 14.

The effluent gas mainly comprising ethylene, benzene fraction (normally containing benzene together with small amounts of toluene and xylene, BTX), carbon monoxide and methane are passed through heat exchanger 18 where they give up their heat content to heat the recycled gas. The temperature of the product stream is reduced to under 300° C.

The product stream is then passed through a benzene scrubbing tower 20 where the benzene fraction possibly containing small amounts of other hydrocarbon oils is dissolved in benzene. The solution then passes to fractionater 22 where the components are separated, suitably by low pressure distillation to separate the benzene fraction from the ethylene and hydrocarbon oils. The benzene solvent is normally returned to the scrubber 20.

After removal of the hydrocarbon oils, benzene fraction and ethylene, the effluent gas contains principally methane and carbon monoxide which may be separated by conventional means. The methane is recycled through heat exchanger 18 and heater 12 to reactor 10. The amount of methane which is recycled is substantially the same as originally introduced to the system. The carbon monoxide may be collected.

The FIGURE illustrates a process in which the carbon monoxide from the scrubber 20 is employed immediately to produce methanol. In accordance with this process the carbon monoxide-methane stream is reacted with steam in steam reformer 24 to produce carbon dioxide and hydrogen. The mixture which contains methane, carbon monoxide and equimolar quantities of carbon dioxide and hydrogen is washed with methanol in methanol washer 26 from which the carbon dioxide is removed and the $H_2/CO$ ratio adjusted to 2:1. This stream then passes through a catalytic convertor 28 in which the hydrogen and carbon monoxide react to form methanol. The unreacted methane is recycled.

The preparation of methanol by the water gas reaction followed by catalytic conversion is a well known, conventional process. It is not, of course, an essential feature of this invention that the carbon monoxide be converted to methanol.

Based on laboratory scale experiments it presently appears that the process of this invention may produce a small excess of methane. If this proves true for production scale processes, the excess methane may be burned to provide heat for any purpose such as drying the wood if necessary or heating the methane.

Table 1, set forth below, shows a preliminary product analysis for the conversion of fir wood in a plant operating at a capacity of 2000 tons of wood per day.

TABLE 1

| Reactor Conditions | | Yields[1] - % Carbon Conversion | |
|---|---|---|---|
| Temp. | 1000° C. | Ethylene | 23% |
| Pres. | 50 psi | Benzene | 13% |
| Particle size | 1 mm | CO | 48% |
| Res. time | 1 sec | Char | 8% |
| Yields of commercial products | | | |
| | Ethylene | 268 tons/day | |
| | Benzene | 930 barrels/day | |
| | Methanol | 3100 barrels/day | |

[1]Based on carbon in wood converted to carbon in product.

Table 2 is a tabulation of the results of a representative selection of experiments on the reaction of methane wood. Wood particulates were entrained in a process gas stream in a one inch tubular reactor under the conditions shown. Further details of the construction of the reactor may be found in Brookhaven National Laboratory Report No. 50698 (Jan., 1977) available from National Technical Information Service, 5285 Port Royal Rd., Springfield, Va., which is hereby incorporated by reference.

Based on these experiments and several others, including those in which the effect of varying the methane to wood feed ratio were studied, the following observations have been made.

1. The yields of ethylene reach a maximum of about 23% based on converted carbon.
2. The yields of benzene fraction containing principally benzene reach a maximum of about 13% based on converted carbon.
3. There does not appear to be appreciable net consumption of methane, and there may even be a small amount of this product produced.
4. The optimum conditions for the production of both ethylene and benzene fraction are reactor pressure of 50 psi, reactor temperature of 1000° C., a residence time of less than one second and a methane to wood feed ratio of approximately 5.
5. The above parameters may be varied to increase the yield of one product at the expense of the other.
6. Decreasing the methane to wood feed ratio, thus forming a more dense phase in the reactor results in decreased yield of ethylene and benzene fraction, but increases the yield of carbon monoxide.

TABLE 2

Flash Methanolysis of Fir Wood

| Run No. | 590 | 590 | 590 | 591 | 591 | 591 | 592 | 592 | 593 | 593 | 593 | 593 | 594 | 594 | 595 | 645 | 646 | 647 |
|---|---|---|---|---|---|---|---|---|---|---|---|---|---|---|---|---|---|---|
| Reactor Temp. (°C.) | 900 | 900 | 900 | 800 | 800 | 800 | 1000 | 1000 | 1000 | 950 | 975 | 1000 | 925 | 975 | 1000 | 1050 | 1050 | 1050 |
| Reactor Press. (psi) | 50 | 50 | 50 | 50 | 50 | 50 | 50 | 50 | 50 | 50 | 50 | 50 | 20 | 20 | 20 | 20 | 20 | 50 |
| Wood Feed Rate (lb/hr) | 0.89 | 0.89 | 0.89 | 0.92 | 0.92 | 0.92 | 0.92 | 0.92 | 0.80 | 0.80 | 0.80 | 0.80 | 0.71 | 0.71 | 0.73 | 0.91 | 2.11 | 1.46 |
| $CH_4$ Feed Rate (lb/hr) | 4.21 | 4.21 | 4.21 | 4.97 | 4.97 | 4.97 | 4.89 | 4.89 | 5.23 | 5.23 | 5.23 | 5.23 | 5.41 | 5.41 | 3.79 | 3.09 | 2.86 | 2.57 |
| Wood Particle Res. Time (sec) | 0.2 | 0.5 | 0.9 | 0.2 | 0.4 | 0.9 | 0.6 | 0.8 | 0.8 | 0.8 | 0.8 | 0.8 | 0.5 | 0.5 | 0.5 | 0.5 | 0.5 | 0.7 |
| Carbon Conv. to Prod. | | | | | | | | | | | | | | | | | | |
| $CH_4$ | | | | | | | | | | | | | | | | | | |
| $C_2H_4$ | 11.3 | 8.9 | 13.0 | 6.5 | 0 | 8.3 | 15.3 | 20.7 | 16.6 | 15.2 | 17.7 | 20.1 | 14.8 | 16.9 | 18.0 | 17.3 | 9.4 | N.D. |
| $C_2H_6$ | 2.2 | 1.9 | 2.2 | 1.8 | 1.3 | 2.2 | 1.1 | 2.0 | 2.2 | 1.5 | 1.1 | 1.5 | 4.0 | 1.5 | 1.4 | 3.4 | 1.8 | 1.5 |
| Total Gas H.C. | 13.5 | 10.8 | 15.2 | 8.3 | 1.3 | 10.5 | 16.4 | 22.7 | 18.8 | 16.7 | 18.8 | 21.6 | 18.8 | 18.4 | 19.4 | 20.7 | 11.2 | |
| BTX | 2.0 | 4.7 | 5.8 | 1.5 | 0.9 | 2.0 | 7.0 | 12.7 | N.D. | 8.9 | 10.0 | 11.9 | 4.5 | 8.5 | 10.3 | 7.8 | 7.1 | 9.5 |
| Oils ($C_9$) | | | 1.4 | | | 10.8 | | 1.0 | | | | | | | | | | |
| Total Liquid H.C. | | | 7.2 | | | 12.8 | | 13.7 | | | | | | | | | | |
| CO | N.D. | N.D. | 47.7 | N.D. | 40.7 | 41.7 | 42.8 | 48.1 | 46.6 | 49.1 | 47.6 | 40.6 | 48.1 | 45.6 | 41.4 | 37.0 | 58.1 | 46.2 |
| $CO_2$ | 2.8 | 3.2 | 2.5 | 2.4 | 3.0 | 2.3 | 2.9 | 3.3 | 3.9 | 3.3 | 3.4 | 3.3 | 2.8 | 2.3 | 2.8 | 2.2 | 2.4 | 2.7 |
| Total $CO_x$ | | | 50.2 | | 43.7 | 44.0 | 45.7 | 51.4 | 50.5 | 52.4 | 51.0 | 43.9 | 50.9 | 47.9 | 44.2 | 39.2 | 60.5 | 48.9 |
| Total Conv. | | | 72.6 | | 45.9 | 67.3 | 69.1 | 87.8 | | 78.0 | 79.8 | 77.4 | 74.2 | 74.8 | 73.9 | 67.5 | 78.8 | 63.1 |

ND — Not Determined

We claim:

1. A process for the production of ethylene in yields greater than 20%, benzene in yields greater than 12%, and carbon monoxide in yields greater than 45% which consists essentially of reacting particulate wood with a particle size up to about 6 mm with added methane in a reactor at a temperature of from about 700° C. to 1200° C. at a pressure of from about 20 psi to 100 psi for a reaction period of from about 0.2 to 10 seconds.

2. A process as in claim 1 wherein the particle size of the wood is from about 0.1 to 6 mm, the temperature is from 900° C. to 1000° C., the pressure is from 30 psi to 60 psi and the reaction period is from 0.2 to 5 seconds.

3. A process as in claim 1 wherein a particulate caking inhibitor is mixed with the wood.

4. A process as in claim 1 wherein silica powder is mixed with the wood.

5. A process as in claim 2 wherein a particulate caking inhibitor is mixed with the wood.

6. A process as in claim 2 wherein silica powder is mixed with the wood.

7. A process as in claim 1 wherein the methane is recirculated to the reactor after the ethylene, benzene and carbon monoxide fractions have been separated from the reaction mixture.

8. A process as in claim 2 wherein the methane is recirculated to the reactor after the ethylene, benzene and carbon monoxide fractions have been separated from the reaction mixture.

9. A process as in claim 1 wherein the carbon monoxide so produced is converted to methanol.

10. A process as in claim 2 wherein the carbon monoxide so produced is converted to methanol.

* * * * *